(12) United States Patent
Ehrenberger et al.

(10) Patent No.: US 6,573,265 B2
(45) Date of Patent: Jun. 3, 2003

(54) USE OF 1-(AMINOALKYL)-3-QUINOXALINE-2-ON DERIVATIVES FOR THE PREPARATION OF COMPOUNDS HAVING AN ANTIOXIDANT ACTION

(75) Inventors: Klaus Ehrenberger, Vienna (AT); Dominik Felix, Zürich (CH); Peter König, Feldkirch (AT); Burkhard Poeggeler, Catonsville, MD (US)

(73) Assignee: Phafag Aktiengesellschaft, Schaanwald (LI)

( * ) Notice: Subject to any disclaimer, the term of this patent is extended or adjusted under 35 U.S.C. 154(b) by 0 days.

(21) Appl. No.: 09/737,741

(22) Filed: Dec. 18, 2000

(65) Prior Publication Data

US 2001/0006966 A1 Jul. 5, 2001

Related U.S. Application Data

(63) Continuation of application No. PCT/AT99/00158, filed on Jun. 17, 1999.

(30) Foreign Application Priority Data

Jun. 19, 1998 (AT) .............................................. 1063/98

(51) Int. Cl.$^7$ ........................... A61P 25/28; A61P 35/00
(52) U.S. Cl. ................................................. 514/249
(58) Field of Search ............................ 514/249; 544/354

(56) References Cited

U.S. PATENT DOCUMENTS 4,339,452 A * 7/1982 Hara et al. ................... 514/249
5,563,140 A * 10/1996 Ehrenberger et al. ....... 514/249

FOREIGN PATENT DOCUMENTS

| DE | 2521905 | 12/1975 |
|---|---|---|
| EP | 0032564 A1 | 7/1981 |
| EP | 0542689 A1 | 5/1993 |

OTHER PUBLICATIONS

Saletu, B.; Grunberger, J.; Anderer, P.; Linzmayer, L.; Konig, P., Br. J. Clin. Pharmacol., 41(2), 89–94 (English) 1996.*
Scaus, J.M. et al, Ann. Rep. Med. Chem., 33, 1998, p 1–10.*
Lewis P. Rowland, M.D., and Neil A. Shneide, "Amyotrophic Lateral Sclerosis", N. Engl. J. Med., vol. 344:1688–1700, May 31, 2001, No. 22,.*
Al–Chalabi A, Leigh PN., "Recent advances in amyotrophic lateral sclerosis", Curr Opin Neurol. Aug. 2000; 13(4):397–405.*
Draetta, G. and Pagano, M. in "Annual Reports in Medicinal Chemistry, vol. 31", 1996, Academic Press, San Diego, p241–246.*
"Cecil Textbook of Medicine, 20th Edition", Bennett, J.C. Editor, W.B. Saunders, Philadelphia, 1996, p. 1957.*
MacLaren RE,: Eye Jun. 1999; 13 (Pt 3a):277–84 Re–establishment of visual circuitry after optic nerve regeneration. Medline Abstract.*
Kuffler D., P R Health Sci J Sep. 2000;19(3):241–52, Medline Abstract.*
Salmon, S.E. et al "Principles of Cancer Therapy" in "Cecil Textbook of Medicine, 20th Edition", W.B. Saunders, Philadelphia, 1996, pp. 1036–1049.*
Balasubramanian, B.N. et al, "Recent Developments in Cancer Cytoxics" in "Annual Reports in Medicinal Chemistry, vol. 33", Academic Press, San Diego, 1998, pp. 151–159.*
Ehrenberger et al, Neuropharmacology, vol. 31, "Caroverine depresses the activity of . . . ", pp. 1259–1263, Dec. 1992.
Saletu et al, British Journal of Clinical Pharmacology, vol. 41, "On the cerebro–protective . . . ", pp. 89–99, Feb. 1996.
Saletu et al, Arzneimittel–Forschung/Drug Research, vol. 45–1, No. 3, "Acute Central Effects . . . ", pp. 217–229, Mar. 1995.
Menke et al, Calcium–Antagonisten in Der . . . , vol. 113, No. 44, "Calcium antagonist in the . . . ", pp. 1728–1732, 1988.
Tsuruo et al, Cancer Research, vol. 43, No. 5, "Potentiation in the vincristine and adriamycin . . . ", pp. 2267–2272, 1983.
Naspitz, Journal of Asthma, vol. 21, No. 6, "Use of calcium channel blocking agents in the . . . ", pp. 451–460, 1984.
Kaik et al, Wiener Medizinische Wochenscrift, vol. 127, No. 1 "Inhalation or peroral therapy . . . ", pp. 22–28, 1977.
Chemical Abstracts No. 99:16559 & JP 58 057317, "Enhancement of neoplasm . . . ", Mitsubishi Chemical Ind. Co. Ltd., Apr. 5, 1983.
Sawada et al, Annals of Neurology, "Dopamine D2–Type Agonists Protect Mesencephalic . . . ", pp. 109–119, Jul. 1998.

* cited by examiner

*Primary Examiner*—Richard Raymond
*Assistant Examiner*—Thomas C. McKenzie
(74) *Attorney, Agent, or Firm*—Jacobson Holman PLLC

(57) ABSTRACT

The invention relates to the use of 1-(aminoalkyl)-3-quinoxaline-2-one derivatives, especially 1-diethylaminoethyl-3-quinoxaline-2-one derivatives of the formula (I), where R 3 is hydroxy, methoxy, ethoxy or hydrogen, or pharmaceutically compatible salts thereof, for the preparation of compounds having an antioxidant action and used for preventing or treating diseases caused by free radicals of the cellular oxygen metabolism, stimulating nerve cell growth, antagonizing glutamate receptors and/or stimulating the growth notably of glutamergic nerve cells.

14 Claims, 4 Drawing Sheets

○ reactivity against hydroxyl radicals
□ reactivity against peroxyl radicals
▲ reactivity against ABTA⁺ radicals

USE OF 1-(AMINOALKYL)-3-QUINOXALINE-2-ON DERIVATIVES FOR THE PREPARATION OF COMPOUNDS HAVING AN ANTIOXIDANT ACTION

The present application is a continuation application of PCT/AT99/00158, filed on Jun. 17, 1999.

BACKGROUND OF THE INVENTION

1. Field of the Invention

The present invention relates to the use of 1-(aminoalkyl)-3-quinoxaline-2-on derivatives and, in particular, 1-diethylaminoethyl-3-quinoxaline-2-on derivatives of the formula

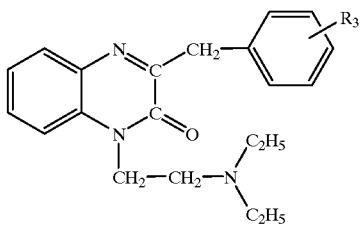

wherein $R_3$ is hydroxy, methoxy, ethoxy or hydrogen, or pharmaceutically acceptable salts thereof, for the preparation of novel pharmaceutical compositions.

2. Description of the Prior Art

The pharmaceutical activity of 1-(aminoalkyl)-3-quinoxaline-2-on derivatives has been known for many years and, in particular, 1-diethylaminoethyl-3-(p-methoxybenzyl)-1,2-dihydroquinoxaline-1-on, whose nonproprietary name is Caroverine, has already been employed as an effective spasmolyticum in the gastrointestinal region. In that case, the efficacy of that substance is attributed, in particular, to its calcium-blocking properties, blocking the calcium-mediated activation of myofibrillar ATP.

EP-A 0 032 564 describes the use of Caroverine or its pharmaceutically safe salts for a plurality of angiocardiopathies and as a preparation for inhibiting platelet aggregation in human blood, as a preparation enhancing blood circulation and also as a substance for treating angina pectoris, myocardial infarctions, hypertonic conditions and the like. The effect of Caroverine in EP-A 0 032 564 was attributed to the fact that it is a specific Ca antagonist and that Caroverine is capable of inhibiting up to 50% of the $Ca_2^+$ ion flux into cells.

In Subsidia med. 22, 3, pages 78–85 (1970) Möslinger reported that Caroverine could suppress epileptic seizures. Also the use of Caroverine in the treatment of acute alcohol withdrawal symptoms and its application in alkaloid withdrawal symptoms have already been described.

From EP-A 0 542 689, the use of 1-(aminoalkyl)-3-quinoxaline-2-on derivatives as neuroprotective substances is to be taken, its use in glutamate-induced and glutamate-receptor-mediated neurotoxic dysfunctions and functional disorders of the central nervous system and, in particular, of the internal ear and of the retina being particularly described. That document also speaks of the use of those substances for treating degenerative processes of neurons in the central nervous system such as, for instance, Alzheimer's disease, Huntington's disease, Parkinson's disease, Wernicke-Korsakoff and Jakob-Creutzfeld syndromes. The action of the specific quinoxaline derivatives mentioned is attributed to the selective blocking of the NMDA and non-NMDA receptors without influencing other receptors such that the pharmaceuticals described in that document appear to be suitable only for application in glutamate-induced and glutamate-receptor-mediated neurotoxic dysfunctions, such as functional disorders of the internal ear and of the retina, and for the degenerative processes mentioned.

From Derwent Abstract, Publication No. AN 83-45789 K, the action of Caroverine and, in particular, 1-(2-dialkylaminoalkyl)-3-(p-alkoxybenzyl)-1,2-dihydroquinoxaline-2-on substances as active substances in the control of the inflow and outflow of anticancer agents can be taken, wherein the anticancer activity is developed as the anticancer agents are transferred into the cells through the cell membranes. With the usual anticancer agents, the effect will decrease in the course of time, because the cancer cells are getting resistant against the same, on the one hand, and the anticancer agents are streaming out of the cancer cells or emerge slowly from the same, on the other hand, which is impeded according to that prior art by the administration of quinoxaline derivatives, since said quinoxaline derivatives [prevent]$_{sic}$ the anticancer agent from flowing out of the cells, thus ensuring the retention of the high concentrations of anticancer agent within the cells.

DE-A 25 21 905 describes a medicament containing 1-diethylaminoethyl-3-(p-methoxybenzyl)-2,1,2-dihydroquinoxaline-2-on, which is said to exhibit effects on the cerebral vessels and the cerebral blood circulation.

SUMMARY OF THE INVENTION

The present invention aims at providing, in addition to the initially mentioned use of specific 1-(aminoalkyl)-3-quinoxaline-2-on derivatives, novel pharmaceutical applications and, therefore, relates to the use of 1-(aminoalkyl)-3-quinoxaline-2-on derivatives and, in particular, 1-diethylaminoethyl-3-quinoxaline-2-on derivatives of the formula

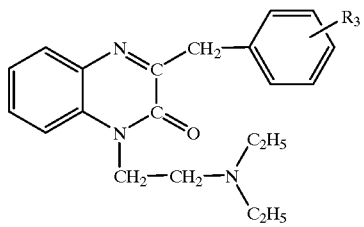

wherein R is hydroxy, methoxy, ethoxy or hydrogen, or pharmaceutically acceptable salts thereof, for the preparation of compositions acting as antioxidants for preventing or treating diseases caused by free radicals of the oxygen cell metabolism, for stimulating the growth of nerve cells, antagonizing glutamate receptors and/or stimulating the growth of, in particular glutamatergic, nerve cells. In extensive studies on the structure of the molecules and their potential mode of action, the Applicant found that the 1-diethylaminoethyl-3-quinoxaline-2-on derivatives used according to the invention were extremely strong antioxidants and that, as a result, they exhibited, in particular, an extremely high capacity as radical interceptors, primarily vis-à-vis the hydroxyl, peroxyl and peroxynitrite radicals, which are responsible for the causation of a plurality of diseases. Their actions as antioxidants and hence as radical interceptors is attributed to the structural conditions inherent in these specific substances, which are quinoxalines with electron-rich aromatic ring systems including redoxoactive oxygen and nitrogen atoms. Due to the large number of electrons available in the molecule, it could be proved that the compounds were able to bind free radicals so as to enable the treatment, or prevent the outbreak, of diseases brought about by free radicals and, in particular, diseases brought about by free radicals of the oxygen cell metabolism, by means of the specific 1-diethylaminoethyl-3-quinoxaline-2-on derivatives used according to the invention. Moreover, it has been shown in a surprising manner that specific 1-(aminoalkyl)-3-quinoxaline-2-on derivatives and, in particular, Caroverine are capable of antagonizing metabotropic glutamate receptors. Since glutamate receptors and, in particular, metabotropic glutamate receptors have been recognized as promoters or catalysts of intracellular metabolism, Caroverine and other 1-(aminoalkyl)-3-quinoxaline-2-on derivatives are capable of antagonizing, i.e., markedly retarding, in particular, that intracellular metabolism.

Since the quinoxaline-2-on derivatives used according to the invention are known to be pharmaceutically applicable without noticeable side effects, attempts were made in the course of the studies to define and optimize the range of action of the substance as an antioxidant and radial interceptor by increasing the dose of administration. During those studies, it was surprisingly found that the 1-(aminoalkyl)-3-quinoxaline-2-on derivatives used according to the invention, in addition to their known activity as neuroprotective substances and on grounds of the antioxidative action discovered in the course of the studies leading to the present invention exhibit a neuroregenerative effect if administered in higher doses. This is because radicals block the intrinsic neurotrophines in a manner that, in case a radical interceptor is applied, neurotrophine activity will be reconstituted and the neuroregenerative action of the substances used according to the invention will commence. It was, therefore, feasible in the course of the studies to not only protect against further destruction damaged nerves and, in particular, nerve paths impaired or destroyed in the course of degenerative processes by neurons occurring in the central nervous system as already stated in EP-B 0 542 689, but to restore the destroyed nerve paths in a manner that, in addition to the known neuroprotective activity of such substances, also a neuroregenerative action surprisingly entered into effect, which resulted in a remarkable reduction of the signs of neurodegenerative diseases and in an improvement in the patients' conditions.

Among the 1-(aminoalkyl)-3-quinoxaline-2-on derivatives used according to the invention, in particular, the hydroxy derivative 1-diethylaminoethyl-3-(p-hydroxybenzyl)-1,2-dihydroquinoxaline-2-on and the methoxy derivative 1-diethylaminoethyl-3-(p-methoxybenzyl)-1,2-dihydroquinoxyline-2-on (Caroverine) show good activities and could be administered in in vitro tests even at elevated dosages without harmful side effects on the assayed cells and in in vivo tests to test animals and patients without harmful side effects.

Due to their strong antioxidative effects, and hence their radical interceptor qualities, the 1-(aminoalkyl)-3-quinoxaline-2-on derivatives used according to the invention are effective, in particular, for preventing or treating DNA alterations caused by free OH radicals and, in particular, cancer. This mode of action goes back to that one of the major biological effects of, in particular, OH radicals and ONNO radicals is the oxidation of DNA with the biological consequence of a mutation of the same and, as a result, the formation of cancer. This mode of action of, in particular, OH radicals has been investigated and demonstrated in a great number of assays. From those assays results that, due to the oncogenous effect of the OH radical on DNA, a potent OH radical interceptor, i.e., an antioxidant capable of inhibiting the oxidative effect of the OH radical on biological material is suitable as an agent for preventing and treating cancerous diseases, as suggested by the invention.

Another preferred mode of action of the 1-(aminoalkyl)-3-quinoxaline-2-on derivatives used according to the invention resides in the treatment of diseases based on viral replication by free radicals of the oxygen cell metabolism and, in particular, in the inhibition of HIV replication. In studies relating to diseases based on viral replication by free radicals of the oxygen cell metabolism it was found that, upon administration of the quinoxaline derivatives used according to the invention and, in particular, Caroverine, the replication of HIV in macrophages derived from monocytes could be markedly reduced on account of the strong radical interceptor qualities of the substances used according to the invention and, in particular, Caroverine.

Due to the strong antioxidative properties of the 1-(aminoalkyl)-3-quinoxaline-2-on derivatives used according to the invention, their application in case of cell ageing manifestations and/or cell destructions, in particular skin ageing manifestations, caused by free radicals of the oxygen cell metabolism has proved to be particularly efficient and successful. That effect occurs both after an oxidative attack on body cells caused by chemicals and with skin cells exposed to a strong oxidizing attack due to environmental influences and, in particular, sunlight.

Allergic reactions and, in particular, type I allergies are caused, for instance, by the attack of histamine, cytokines, lipid mediators and neuromediators and currently are treated by administering antihistamines. It has now been surprisingly found that, by the exposure to histamines, cytokines, lipid mediators and neuromediators, peroxynitrite and OH radicals are released and that, by applying the 1-(aminoalkyl)-3-quinoxaline-2-on derivatives used according to the invention, the occurrence of secondary effects of allergies such as, e.g., inflammations and the like can be completely avoided, and also primary manifestations such as, e.g., sneezing can be stopped almost immediately upon administration of the 1-(aminoalkyl)-3-quinoxaline-2-on derivatives used according to the invention, because of their antioxidative properties and, in particular, radical interceptor properties.

A particularly surprising and therapeutically particularly interesting application of the 1-(aminoalkyl)-3-quinoxaline-2-on derivatives used according to the invention is provided by the latter being suitable for stimulating the growth of nerve cells, in particular for restoring the functionability of, in particular glutamatergic, nerves after a cerebral stroke as well as for improving dysphagia, disturbed articulation and, in particular, speech disorders and transverse lesions of the cord with paraplegia, for treating Alzheimer's disease, schizophrenia or amyotrophic lateral sclerosis, and for stimulating nerve growth with a cochlear implant as well as in case of functional deficits of the auditory nerve, balancing nerve, optic nerve, olfactory nerve or facial nerve.

In the course of investigations of the dosages in which the quinoxaline derivatives used according to the invention may be pharmaceutically administered to patients without serious side effects, it was surprisingly found, as already pointed out above, that the substances, in addition to their known neuroprotective action, particularly exhibit neuroregenerative actions such that the use of the compositions according to the invention in case of diseases based on the degeneration of, in particular glutamatergic, nerve cells enables the clinical picture not only to be kept stationary, as has been shown in the prior art, but, according to the invention, to be clearly improved in any event while ensuring new nerve cell growth.

It was, thus, determined, in particular in patients carrying cochlear implants for stimulating the nerves in the internal ear, that, when simultaneously administering the quinoxaline-2-on derivatives used according to the invention and, in particular Caroverine, the nerve stimulated by the implant was partially regenerated and, thereby, contacting of the implant was markedly improved, thereby clearly enhancing the audition of the thus treated patients.

It turned out to be particularly advantageous that the 1-(aminoalkyl)-3-quinoxaline-2-on derivatives or their pharmaceutically acceptably salts, if used as antioxidants and, in particular, as radical interceptors, are applied at a daily dose ranging from 3 to 10 mg/kg and, in particular, 5 to 10 mg/kg body weight. By administering such a dose, it is feasible to markedly reduce or alleviate the symptoms of the disease without involving the occurrence of side effects due to the dosage of the medicament.

When applying the 1-(aminoalkyl)-3-quinoxaline-2-on derivatives used according to the invention, or pharmaceutically acceptable salts thereof, as neuroregenerative substances, preferably a daily dose of 3 to 20 mg/kg body weight and, in particular, 5 to 15 mg/kg body weight is employed.

At low dosages and, in particular, dosages known from the literature, of the substances and, in particular, Caroverine as neuroregenerative substance, as a calcium antagonist or even as an antioxidant, as proposed by the invention, tests and, in particular, in vitro tests have shown no neuroregenerative effect of the substance such that a high dose of the substance must be applied for obtaining the neuroregenerative effect to be reached according to the invention. In appropriate tests it was ascertained that even the high dosages proposed by the invention may be administered to patients with hardly any side effect.

The 1-(aminoalkyl)-3-quinoxaline-2-on derivatives used according to the invention may be administered in any known formulation and, in particular, orally, transdermally, topically and parenterally, intravenous administration appearing to be preferred except when used as an agent for preventing the premature ageing of skin cells.

SHORT DESCRIPTION OF THE DRAWINGS

In the following, the invention will be explained in more detail by way of experiments and exemplary embodiments with reference to the accompanying drawings, wherein.

DETAILED DESCRIPTION OF PREFERRED EMBODIMENTS OF THE INVENTION

EXAMPLES 1, 2 AND 3

By way of clinical examples, the efficacy of Caroverine (1-diethylaminoethyl-3-(p-methoxybenzyl)-1,2-dihydroquinoxaline-2-on) as a neuroregenerative substance was tested in two patients suffering from a severe sudden loss of hearing.

Figure 1:
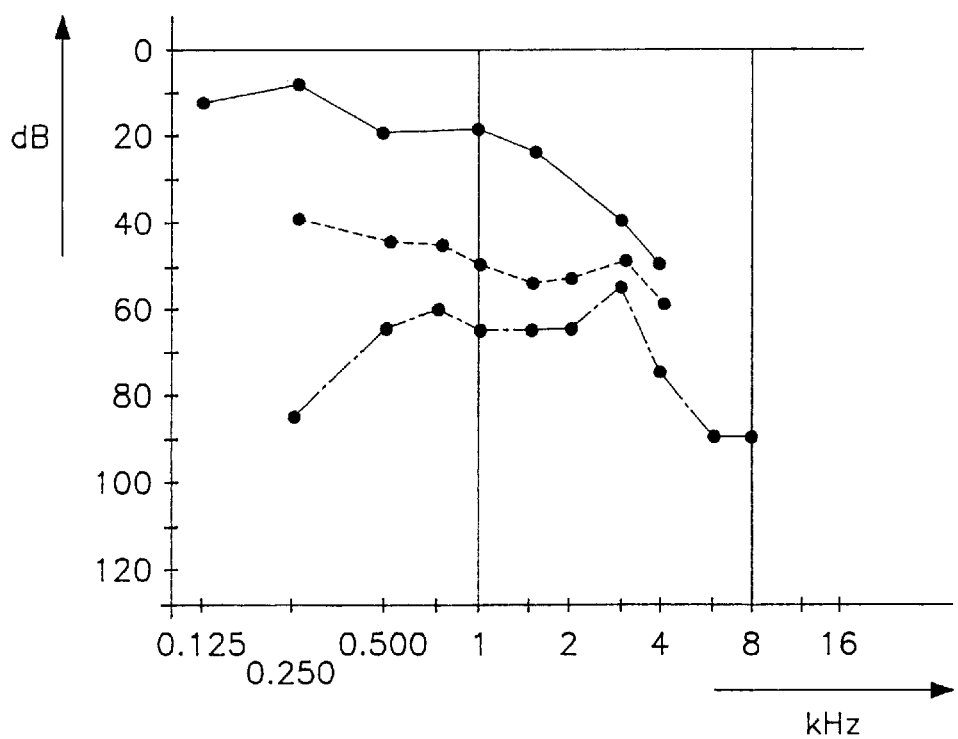
FIG. 1 is a sound audiogram of a female patient.

In the enclosed diagram of FIG. 1, the sound audiogram of a female patient is shown, the dot-and-dash line illustrating the sound audiogram after a sudden loss of hearing, the broken line illustrating the sound audiogram immediately upon commencement of the treatment, and the full line illustrating the patient's sound audiogram two weeks after the beginning of treatment, the patient over that period having been treated by the administration of an elevated dose of Caroverine. 240 mg Caroverine dissolved in 250 ml physiological saline were each slowly administered intravenously three times a day.

The marked increase in the hearing performance of the patient goes back to the at least partial restoration of the auditory nerve.

Figure 2:
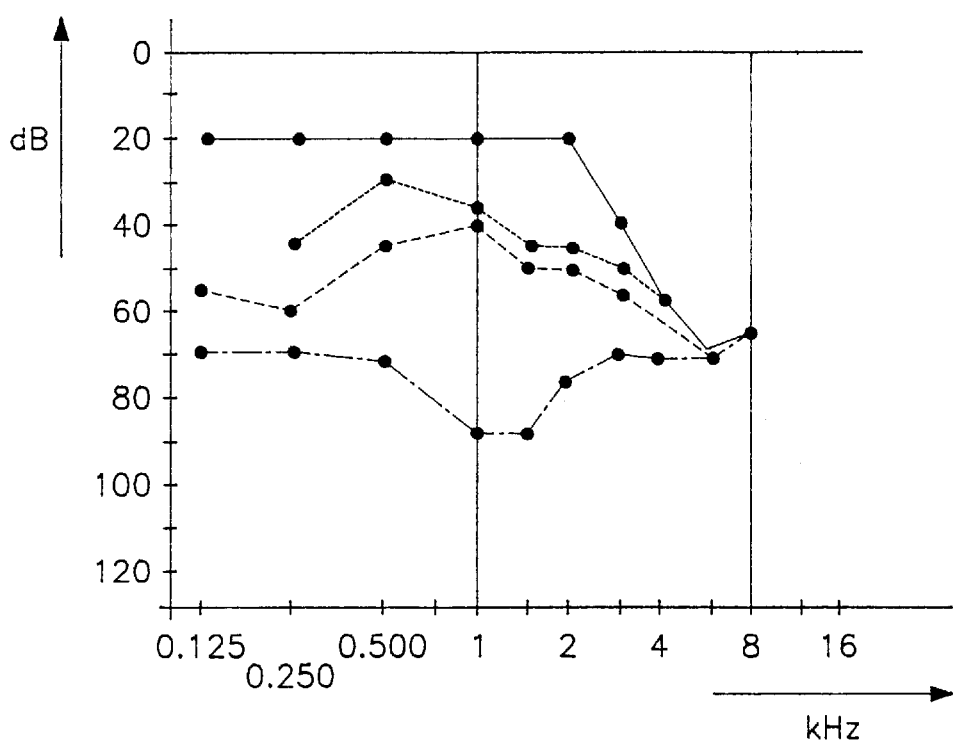
FIG. 2 is a sound audiogram of a male patient.

FIG. 2 shows an analogous example by way of a male patient, wherein, again, the dot-and-dash line shows the patient's audiogram after the sudden loss of hearing and before the beginning of treatment and prior to the insertion of a cochlear implant, the broken line shows the patient's audiogram after the administration of low doses of Caroverine, the dotted line shows the patient's audiogram after a two-week treatment by administering elevated doses of Caroverine and the full line again shows the patient's audiogram after a two-week administration of high doses of Caroverine and after the insertion of a cochlear implant. It is clearly apparent from FIG. 2 that the administration of low doses of Caroverine, i.e., 160 mg Caroverine three times a day, is able to improve the patient's hearing performance, which improvement is, however, little significant. If the patient is administered 240 mg/250 ml physiological saline, of Caroverine four times a day over a period of two weeks and a cochlear implant is additionally inserted, a stable hearing performance in a frequency range of between 0.125 and 2 kHz will be reached, which nearly corresponds to the hearing performance of a healthy individual.

Figure 3:
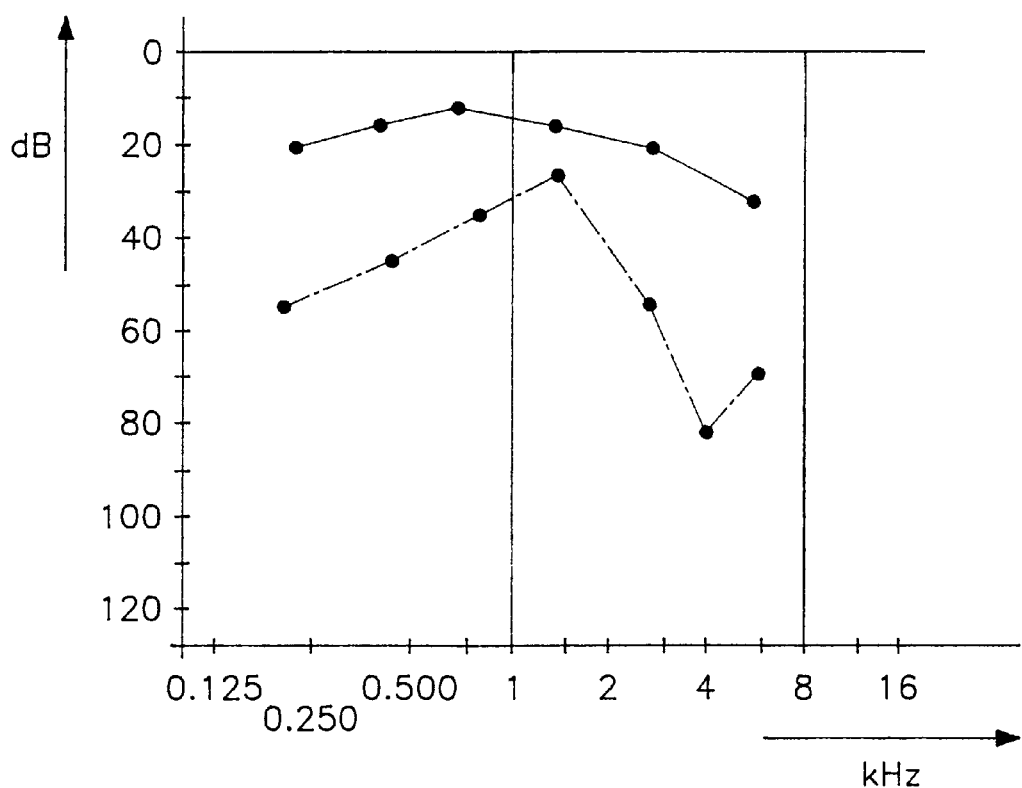
FIG. 3 is a sound audiogram of another male patient.

FIG. 3 illustrates a further example by way of a male patient, wherein, again, the dot-and-dash line shows the patient's audiogram after a sudden loss of hearing and before the beginning of a treatment and the full line shows the patient's diagram after a two-week treatment with elevated doses of Caroverine. A cochlear implant was not inserted. From FIG. 3 it is clearly apparent that, by the administration of elevated doses of Caroverine, with 300 mg Caroverine in 500 ml physiological saline being administered each day over a period of two weeks in the instant case, a stable hearing performance in the frequency range of between 0.250 and 8 kH can be reached, which essentially corresponds to the hearing performance of a healthy individual.

From the data of FIGS. 1, 2 and 3 it is clearly apparent that Caroverine at elevated doses is able to act neuroregeneratively as opposed to the known administrations and that, in particular, patients additionally carrying cochlear implants exhibit markedly improved hearing performances due to the enhanced contact of the implant with the auditory nerve.

EXAMPLE 4

By way of two male patients aged between 70 and 75 and suffering from Alzheimer's disease, the effect of Caroverine as a neuroregenerative substance was further investigated. The patients had average body weights of 75 kg and were in-patients. Three times a day the patients were each administered 400 mg Caroverine in physiological saline as an infusion over a period of about 2 hours, wherein usual additives could be admixed to said infusion solutions. The time of treatment in each case was maintained for three weeks.

Prior to beginning of the treatment with elevated doses of Caroverine, the patients were forgetful, did not recognize their nearest relatives and were considered as persons in need. At the end of the treatment period of three weeks a marked improvement in the conditions of the two patients was to be noted, they were partially able to eat again by themselves and recognized their nearest relatives and the nursing staff. Bearing in mind that the known substances used for the treatment of Alzheimer's disease merely are able to bring about a stabilization of the condition, the effect of Caroverine apparently is to be attributed to the neuroregenerative action of the substance such that certain neurologically controlled functions could be learned anew to a certain extent within a relatively short period of administration.

Also with the intravenous administration of 160 mg Caroverine in 250 ml saline, each three times a day over a period of three weeks improvements in the patients' conditions could be achieved, yet observations were not as pronounced and sustained, from which it may be immediately concluded that a lasting therapeutical success will be achieved only if the neuroregenerative action of Caroverine enters into effect.

EXAMPLE 5

4 patients, two female and two male patients, aged between 40 and 50 and suffering from periodic schizophrenia were treated with elevated doses of Caroverine during massive attacks. They were each administered 400 mg Caroverine in physiological saline in the form of an infusion for a period of approximately 30 minutes three times a day. The treatment time was 7 days, 14 days and 21 days, respectively.

Immediately upon the beginning of the treatment with elevated doses of Caroverine, all of the four patients exhibited marked improvements in their behaviors. They showed a noticeable brightening up, hardly any hallucinations and were able to both recognize real facts and act accordingly, were cooperative and able to do their daily businesses without being extremely strained and disoriented.

In all of the four patients it turned out that those improvements in their conditions lasted over the period of treatment, yet only that patient whose treatment time was 21 days was successful even beyond the treatment time.

Unlike existing methods of treatment, a significant improvement in the patients' behaviors was shown during the period of treatment, wherein, moreover, the serious side effects usually occurring upon the administration of psychopharmacological agents, such as apathetic conditions, weight gains and the like, could be avoided by the administration of Caroverine.

By administering a daily dose of 240 mg Caroverine or 400 mg Caroverine in combination with 10 mg Haloperidole (a neurolepticum from the class of butyrophenones), results analogous to those of the higher-dose administration of Caroverine could be achieved, wherein the improvements in the conditions did not continue as the administration of Caroverine was stopped.

EXAMPLE 6

The neuroregenerative action of Caroverine was further investigated by way of two patients suffering from facial nerve paralysis.

Two female patients suffering from a serious paralysis of the trigeminus nerve were treated with Caroverine in the form of a combined cure over a period of 4 weeks, wherein, on the one hand, Caroverine was applied three times a day by intravenously administering 360 mg Caroverine each and the active substance, in addition, was administered in the form of a depot plaster containing 1000 mg Caroverine. The depot plaster was replaced once a week. Already after 2 weeks, an improvement in the signs of paralysis could be observed in each of the patients to the extent that the paralyzed face half started to show traces of mimicry and the patients were again able to control, in particular, their eye lids as they liked.

Further extension of the period of treatment with Caroverine resulted in additional reductions of the paralytical signs, wherein it turned out, however, that a complete restoration of the function of the facial nerve merely by the treatment with Caroverine was not readily feasible.

EXAMPLE 7

Figure 4:
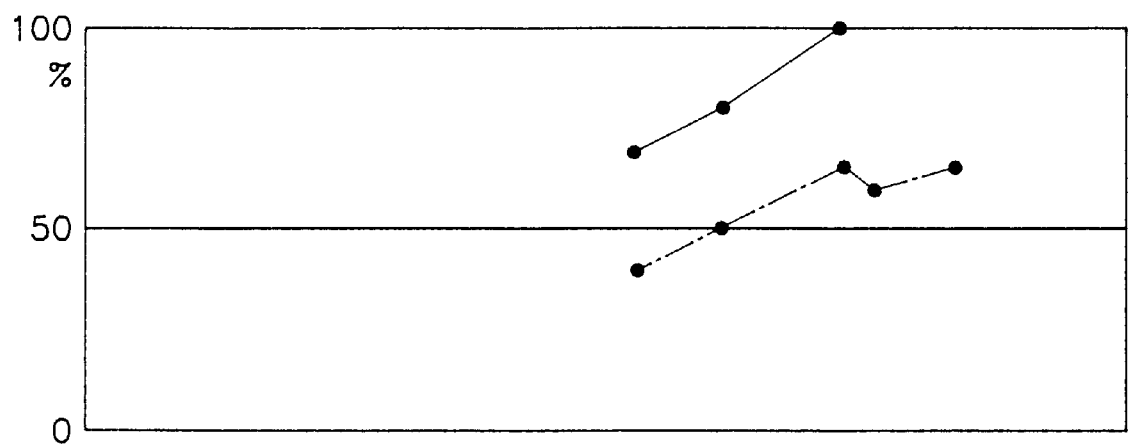
FIG. 4 is a speech and articulation diagram of a male patient.

A patient suffering from serious speech impediments due to a stroke was intravenously administered Caroverine over a period of 3 months at an elevated dose of 4×160 mg Caroverine in physiological saline per day. As is apparent from the annexed FIG. 4, the patient had an approximately 50% articulation capacity at the beginning of treatment, which may be taken from the dot-and-dash line in the diagram, wherein he had regained his 100% articulation capacity (full line in FIG. 4) after the end of treatment, no speech impediments having been observed any more. In respect of the regression of the speech impediments, it was proved that the respective nerves responsible of the articulation capacity had been restored by the neuroregenerative action of Caroverine and hence the complete recovery of the faculty of speech could be achieved.

EXAMPLE 8

Figure 5:
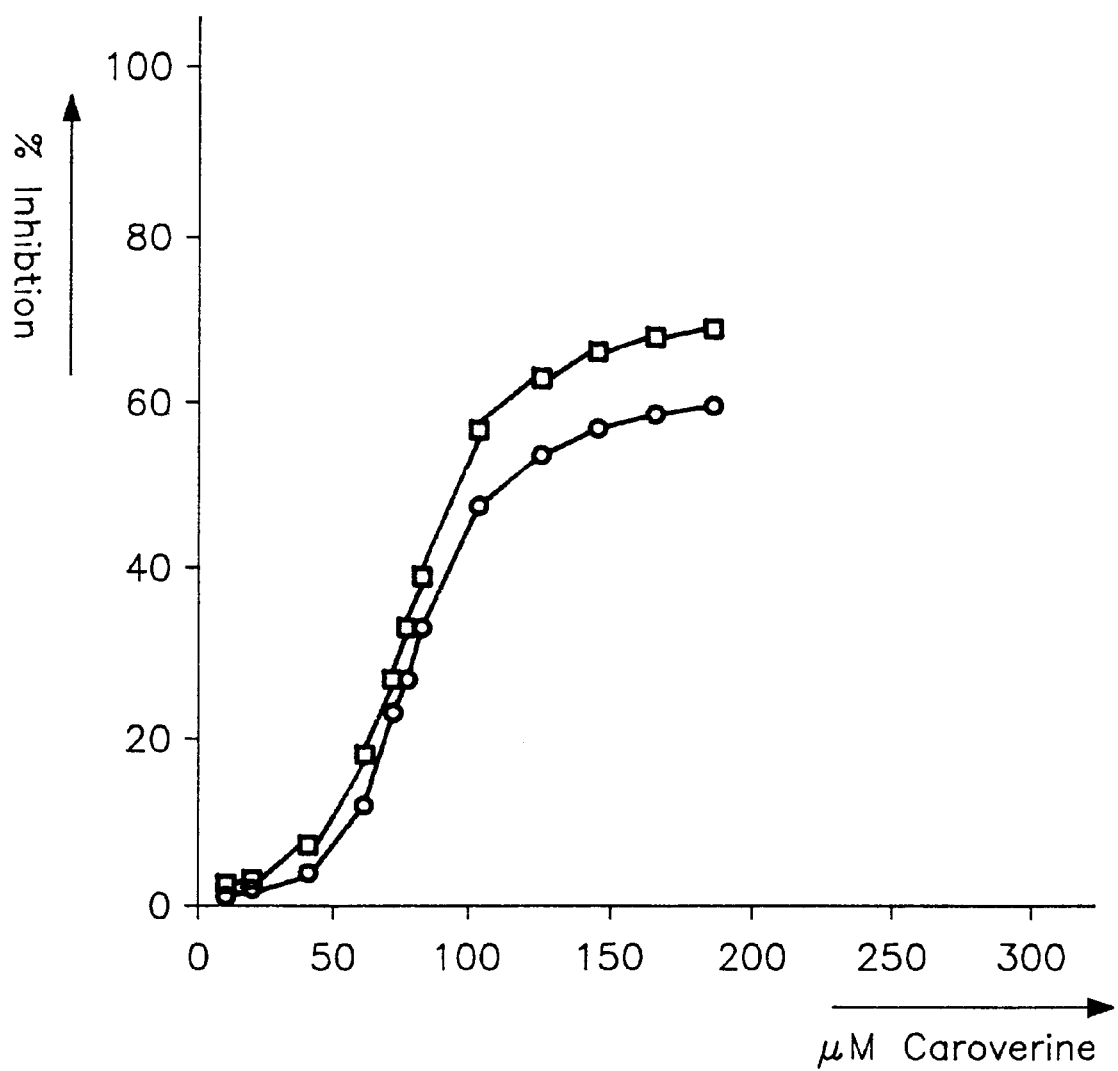
FIG. 5 illustrates the inhibition of the ABTA cation radical by Caroverine.
Figure 6:
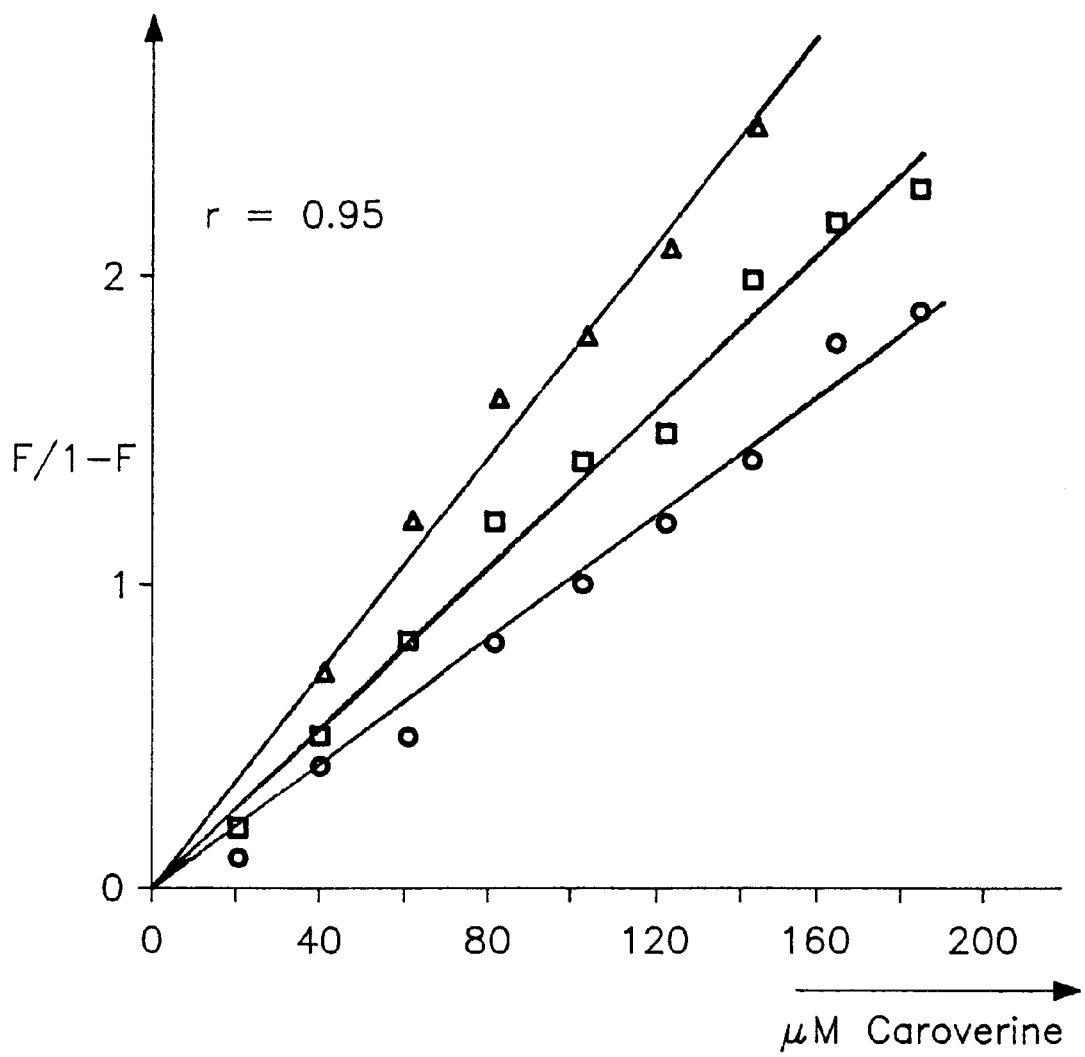
FIG. 6 shows comparative kinetic studies relating to the reactivity of Caroverine against radicals.

In respect of the antioxidative effect of 1-(aminoalkyl)-3-quinoxaline-2-on derivatives and in respect of their radical interceptor properties, in vitro tests were carried out with Caroverine and the specific radical intercepting reagent 2,2'-azino-bis(3-ethylbenz)thiazoline-6-sulfonic acid (ABTA) in order to compare the radical interceptor property of Caroverine with that of ABTA. In the presence of highly reactive radicals, ABTA is oxidized to the stable thiazoline cation radical ABTA$^+$. The intensive green color of that radical was photometrically measured with a main absorption band at 420 nm. Caroverine was able to inhibit the formation of the ABTA cation radical due to the formation of hydroxyl and peroxyl radicals both in the absence and in the presence of cerebral homogenate (FIG. 5). Caroverine reacted rapidly with free hydroxyl, peroxyl and ABTA cation radicals, as was shown in comparative studies with ABTA in the absence and in the presence of cerebral homogenate. The rate constant for the reaction with hydroxyl radicals was $0.4 \times 10^{10}$ M/l/s and that for peroxyl radicals was $0.5 \times 10^{10}$ M/l/s, as was realized by comparative kinetic studies with ABTA in the absence or in the presence of cerebral homogenate (FIG. 6). These results show that Caroverine inhibits ABTA cation radical formation and catalyzes ABTA cation radical reduction in the presence and in the absence of cerebral homogenate and, thus, is highly active as an electron donor in low, micromolar concentrations. In doing so, ABTA cation radical formation and reduction were applied, as already mentioned, in order to examine the single electron transfer reactions, since that substance enables direct measurements of radical formation and radical reduction on account of its color.

In comparative studies it was found that Caroverine is at least three times as effective as the known antioxidants Ascorbate, Trolox and Glutathione. In terms of radical interceptor property, Caroverine was found to reach that of Melatonine, which has been the most effective electron donor and radical interceptor detected to date. For that reason, Caroverine is supposed to be able to facilitate the repair of long-lived organic radicals and damaged biomolecules.

EXAMPLE 9

5 patients, 2 female and 3 male patients, suffering from type I allergy, namely hay fever, were treated with Caroverine at the occurrence of allergical primary reactions, i.e., sneezing, cervical irritations as well as rhinorrhea. They each received one tablet containing 150 mg Caroverine three times a day.

In all of the five patients the occurrence of secondary manifestations of the allergic reactions, i.e., cervical rubor and the like could be avoided. Also the primary reactions such as sneezing, rhinorrhea and the like had completely disappeared after a two-day administration of Caroverine, Caroverine having been administered two times a day at low doses for another week after the disappearance of the primary reactions for maintaining its effect.

For comparative reasons, two patients were treated with usual antihistamines, wherein both the primary manifestations of the allergy and, in particular, the secondary manifestations could not be suppressed immediately and completely such that the patients were suffering from their disease hay fever substantially as long as straining by the causers, namely grass pollens, was maintained. Nor was it possible to discontinue the administration of the medicament as long as pollen flight was observed.

The action of Caroverine in the instant case is based on its extremely high antioxidative effect and, in particular, on its radical interceptor properties selectively reacting, and thus neutralizing, the OH radicals and ONOO radicals produced by the histamines and cytokines, respectively. By the administration of Caroverine, the allergic cycle was interrupted and no further reactions occurred.

EXAMPLE 10

The antioxidative action and, in particular, the action in respect of the premature ageing of skin cells was investigated by preparing an ointment formulation containing 150 mg Caroverine per 100 g cream. Glycerin was used as the cream base; further pharmaceutically active additives were not contained in the cream formulation.

Five female test persons aged between 35 and 45 and, on an average, having dry skins already partially exhibiting clear signs of ageing, used the Caroverine-based cream over a period of 4 weeks, twice a day, both as a make-up base and as a sole night cream.

Already after two weeks marked improvements in the skin appearance were to be observed particularly with the younger test persons, wherein, in particular, sun injuries to the skin as well as red skins caused by oxidation had clearly decreased. Moreover, a somewhat firmer and smoother skin was observed after four weeks.

Even the elderly test persons showed clear skin appearances after four weeks, in particular red skins and sun injuries having been made to disappear almost completely.

EXAMPLE 11

Use of 1-(aminoalkyl)-3-quinoxaline-2-on derivatives as antagonists of the metabotropic group I glutamate receptors in the ear of guinea pigs.

A group of six guinea pigs was injected hydroxyphenyl glycerin as a receptor agonist into the ear, the receptor responding in a manner so as to strongly increase the auditory performance of the guinea pigs. Guinea pigs that have been injected hydroxyphenyl glycerin are scared already at extremely low noises, running nervously around within their cage, and at noises that do not exceed the regular noise level prevailing in a pharmaceutical-chemical laboratory a behavior is observed with some of the guinea pigs, from which the sensation of pain by the animal may be concluded. Four of the six guinea pigs were subsequently injected a dose of 8 mg/kg body weight of the guinea pig into the vein of the ear and the behavior of the guinea pigs was observed. Surprisingly, it has been shown that the guinea pigs calmed down immediately upon the administration of Caroverine and no longer reacted anxiously upon loud noises, such as clapping, in their immediate vicinity. Thus, the guinea pigs did not run away and did not hide in their sleeping caves if clapping occurred directly in front of their cage. By contrast, the two guinea pigs that did had not received Caroverine remained extremely excited and, for instance, clapping in front of their cage caused them to rapidly run to and fro in their cage, exhibiting clear signs of pain and nervousness. These behavioral peculiarities of the guinea pigs were also observed by applying electrodes to the ears of the animals, from whose measured data it could be readily read whether the exposure of the animals to unexpected noises caused excitement or not. Also the measured data of the electrodes clearly showed that excitement was effected not at all or only to an extremely slight extent after the administration of Caroverine to the guinea pigs.

Furthermore, the inhibiting influence of Caroverine on the metabotropic group I glutamate receptors was investigated on the narcotized animal by applying microelectrodes to the auditory nerve. From the results measured on test animals after Caroverine administration and on control animals without Caroverine administration it could be seen that the excitability of the metabotropic group I glutamate receptors was strongly suppressed by the administration of Caroverine.

From these test results it may be concluded that Caroverine and hence 1-(aminoalkyl)-3-quinoxaline-2-on derivatives are able to antagonize metabotropic glutamate receptors in the ears of guinea pigs.

EXAMPLE 12

Use of 1-(aminoalkyl)-3-quinoxaline-2-on derivatives for preventing skin cancer in guinea pigs.

A group of six guinea pigs was shaved in the neck region and exposed to intensive UV irradiation over a period of at least two hours per day. The UV irradiation contained portions of both UV-A and UV-B and UV-C rays. A highly concentrated solution of Caroverine.hydrochloride was brushed on the shaved neck regions of four of the six guinea pigs prior to the commencement of the first irradiation, wherein attention was paid to that the distribution was effected as uniform as possible and over all of the irradiated zone.

After two weeks of intensive irradiation the guinea pigs of the control group exhibited clear skin injuries such as burns, reddening and surfacial skin lesions, wherein during sampling cancer cells were already detectable in the tissue samples. After the same period of irradiation the four guinea pigs treated with the Caroverine.hydrochloride solution did show some reddening of the skin, yet no cancer cells could be detected in the tissue samples taken.

An analogous experiment was carried out with 1-diethylaminoethyl-3-(p-hydroxybenzyl)-1,2-dihyroquinoxaline-2-on with an identical result having been obtained.

From the above follows that the 1-diethylaminoethyl-3-quinoxaline-2-on derivatives used according to the invention are extremely active antioxidants and radical interceptors for radicals of the oxygen cell metabolisms and that, due to that property, they are capable of preventing DNA alterations caused by free radicals, in particular cancer, thus appearing to be suitable for the prevention of, in particular, skin cancer.

EXAMPLE 13

Three patients aged between 19 and 75 and suffering from carcinoma of the colon were additionally administered Caroverine beside the usual chemotherapy with Irinothekam and Oxaliplatine for the four-week period of chemotherapy, the administration on day 1 having been effected at an elevated dose, i.e., intravenously in physiological saline, and on the other days by administering 3×3 tablets a day.

Due to the extremely high antioxidative action of Caroverine, the complete disappearance of the colon carcinoma could be observed in that study. Two control patients not treated with Caroverine showed the known shrinkage of the carcinoma in the chemotherapy, yet disappearance of the same was not feasible.

Other tests in patients suffering from advanced head and throat tumors showed similar results, those patients also having received Caroverine beside the regular chemotherapy. In addition to a successful palliation, also a reduction of the tumor size could be achieved. No complete disappearance of the tumors was feasible.

To sum up, it may be concluded that, due to the extremely high antioxidative action of Caroverine, free radicals of the oxygen cell metabolism are eliminated from the system, thereby preventing continued permanent DNA alteration, which causes cancer. Caroverine, thus, appears not only suitable for preventing cancer, but, in particular, highly effective for treating some specific types of tumors.

What is claimed is:

1. A method of treating a disease in a subject comprising administering to the subject a 1-diethylaminoethyl-3-quinoxaline-2-on derivative of the formula

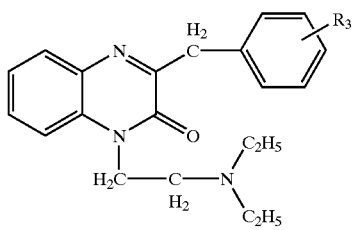

wherein $R_3$ is hydroxy, methoxy, ethoxy or hydrogen, or a pharmaceutically acceptable salt thereof, wherein the disease is selected from the group consisting of schizophrenia, facial nerve paralysis, speech impediment due to a stroke, type I allergies, sudden hearing loss, olfactory disorders, colon cancer, and skin cancer.

2. The method of claim 1, wherein $R_3$ is methoxy.
3. The method of claim 1, wherein $R_3$ is hydroxy.
4. The method of claim 1, wherein free radicals cause the disease.
5. The method of claim 1, wherein the disease includes cellular ageing or cellular destruction and is due to free radicals.
6. A method of treating a symptom of a type I allergy or AIDS in a subject comprising administering to the subject a 1-diethylaminoethyl-3-quinoxaline-2-on derivative of the formula

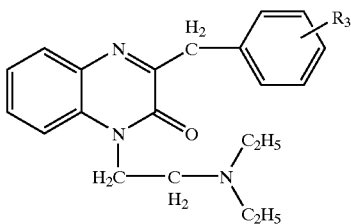

wherein $R_3$ is hydroxy, methoxy, ethoxy or hydrogen, or a pharmaceutically acceptable salt thereof.

7. A method for restoring the functionability of a non-functional nerve due to a cerebral stroke, or improving dysphagia, disturbed articulation, speech disorders and transverse lesions of the cord with paraplegia, or treating schizophrenia, or stimulating nerve growth in a cochlear implant, an auditory nerve, a balancing nerve, an olfactory nerve, or a facial nerve in a subject comprising administering to the subject a 1-diethylaminoethyl-3-quinoxaline-2-on derivative of the formula

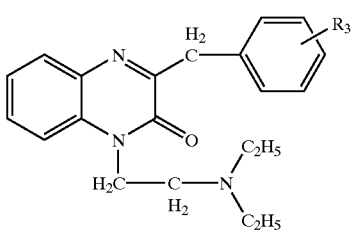

wherein $R_3$ is hydroxy, methoxy, ethoxy or hydrogen, or a pharmaceutically acceptable salt thereof.

8. The method of claim 1, wherein a daily dose of 3 to 20 mg/kg body weight of the 1-diethylaminoethyl-3-quinoxaline-2-on derivative or a pharmaceutically acceptable salt thereof is administered to the subject.

9. The method of claim 1, wherein a daily dose of 5 to 10 mg/kg body weight of the 1-diethylaminoethyl-3-quinoxaline-2-on derivative or a pharmaceutically acceptable salt thereof is administered to the subject.

10. The method of claim 1, wherein the 1-diethylaminoethyl-3-quinoxaline-2-on derivative or a pharmaceutically acceptable salt thereof is administered orally, topically, parenterally, or intravenously.

11. A method for stimulating the growth of peripheral nerve cells in a subject in need thereof which comprises administering to the subject a 1-diethylaminoethyl-3-quinoxaline-2-on derivative of the formula

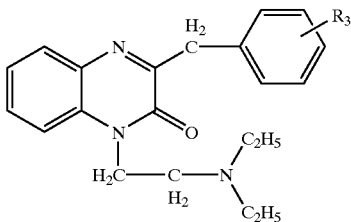

wherein $R_3$ is hydroxy, methoxy, ethoxy or hydrogen, or pharmaceutically acceptable salt thereof.

12. The method of claim 11, wherein the nerve cells are glutamatergic nerve cells.

13. The method of claim 5, wherein the cell is a skin cell.

14. The method of claim 1, wherein a daily dose of 5 to 15 mg/kg body weight of the 1-diethylaminoethyl-3-quinoxaline-2-on derivative or a pharmaceutically acceptable salt thereof is administered to the subject.

* * * * *